US011886614B2

(12) United States Patent
Hanson et al.

(10) Patent No.: US 11,886,614 B2
(45) Date of Patent: Jan. 30, 2024

(54) SYSTEM AND METHOD FOR SECURELY ACCESSING AND DISPLAYING INFORMATION ON A DISPLAY DEVICE HAVING MULTIPLE DISPLAY WINDOWS

(71) Applicant: ShareSafe Media, LLC, Mobile, AL (US)

(72) Inventors: Robert B Hanson, Mobile, AL (US); Dean Kei Naritoku, Mobile, AL (US); Peter Pronovost, Novelty, OH (US)

(73) Assignee: ShareSafe Media, LLC, Mobile, AL (US)

( * ) Notice: Subject to any disclaimer, the term of this patent is extended or adjusted under 35 U.S.C. 154(b) by 0 days.

(21) Appl. No.: 17/777,119

(22) PCT Filed: Jul. 8, 2021

(86) PCT No.: PCT/US2021/040839
§ 371 (c)(1),
(2) Date: Dec. 8, 2022

(87) PCT Pub. No.: WO2022/256023
PCT Pub. Date: Dec. 8, 2022

(65) Prior Publication Data
US 2023/0359761 A1    Nov. 9, 2023

Related U.S. Application Data

(60) Provisional application No. 63/195,594, filed on Jun. 1, 2021.

(51) Int. Cl.
*G06F 21/62* (2013.01)
*G06T 11/60* (2006.01)
(Continued)

(52) U.S. Cl.
CPC .......... *G06F 21/6245* (2013.01); *G06T 11/60* (2013.01); *G16H 10/60* (2018.01);
(Continued)

(58) Field of Classification Search
CPC .... G16H 10/60; G16H 40/67; G06F 21/6245; G06T 11/60; G06T 2200/24; G06T 2210/41
See application file for complete search history.

(56) References Cited

U.S. PATENT DOCUMENTS 7,343,565 B2 *   3/2008   Ying ..................... G06F 3/0488
                                                            715/780
9,003,319 B2 *   4/2015   Linthicum ............. G16H 40/63
                                                            715/777
(Continued)

FOREIGN PATENT DOCUMENTS

JP    2018106553 A    12/2016
JP    2016224536 A    7/2018
(Continued)

OTHER PUBLICATIONS

NPL Search Terms (Year: 2023).*
(Continued)

*Primary Examiner* — Syed A Zaidi
(74) *Attorney, Agent, or Firm* — AdamsIP, LLC; Edward Brinkley Garner, III; James Hunter Adams

(57) ABSTRACT

A system and method for securely displaying patient data within a plurality of display windows of a display user interface is provided. Generally, a user may activate an access computing device by logging into a user profile via a first user interface of a first computing device and scanning a predefined pattern of said access computing device using a camera of the first computing device. If the system recognizes the predefined pattern and the user profile has the appropriate permission levels, a computer readable signal containing login credentials may be sent to the access computing device, allowing the user to access data of the system. In some embodiments, a user may activate a display by logging into a user profile having appropriate permissions and scanning a predefined pattern of the display. The user may use user interfaces of the system to control a plurality of display windows within the display user interface.

13 Claims, 13 Drawing Sheets

(51) Int. Cl.
*G16H 40/67* (2018.01)
*G16H 10/60* (2018.01)

(52) U.S. Cl.
CPC ......... *G16H 40/67* (2018.01); *G06T 2200/24* (2013.01); *G06T 2210/41* (2013.01)

(56) References Cited

U.S. PATENT DOCUMENTS

| | | | |
|---|---|---|---|
| 2002/0177758 A1* | 11/2002 | Schoenberg | G16H 40/63 |
| | | | 600/300 |
| 2004/0001092 A1* | 1/2004 | Rothwein | G06F 8/38 |
| | | | 715/763 |
| 2013/0151266 A1 | 6/2013 | Randall et al. | |
| 2014/0173507 A1* | 6/2014 | Demeyere | G06F 3/1446 |
| | | | 715/789 |
| 2017/0132300 A1* | 5/2017 | Sekar | G06F 16/254 |

FOREIGN PATENT DOCUMENTS

| | | |
|---|---|---|
| JP | 2020123106 A | 6/2020 |
| JP | 2020095592 A | 8/2020 |

OTHER PUBLICATIONS

Appl. No. PCT/US21/040839, filed Jul. 8, 2021, International Search Report, dated Mar. 31, 2022.
Appl. No. PCT/US21/040839, filed Jul. 8, 2021, Written Opinion of the International Searching Authority, dated Mar. 31, 2022.

\* cited by examiner

SYSTEM AND METHOD FOR SECURELY ACCESSING AND DISPLAYING INFORMATION ON A DISPLAY DEVICE HAVING MULTIPLE DISPLAY WINDOWS

CROSS REFERENCES

This application is a U.S. National Stage application of PCT Application Number PCT/US21/40839, filed on Jul. 8, 2021, which claims the benefit of U.S. Provisional Application No. 63/195,594, filed on Jun. 1, 2021, which applications are incorporated herein in their entirety by reference.

FIELD OF THE DISCLOSURE

The subject matter of the present disclosure refers generally to a system and method for quick, secure access to an electronic health record as well as assist with the presentation of information to a patient.

BACKGROUND

Healthcare facilities are increasingly focusing on enhancing a patient's treatment experience by way of technology. This allows said healthcare facilities to differentiate their services from those of competing healthcare facilities as well as improve patient satisfaction ratings, which may increase the number of patients who choose their services over said competing healthcare facilities. In particular, by investing in technology that improves nurse/patient interaction, increases safety, reduces readmissions, and reduces cost to the patient, healthcare facilities have greatly increased quality of care and efficiency of the workforce without also greatly increasing costs. For instance, healthcare facilities are already using televisions as a way to assist patients in learning about their conditions. Interactive patient education systems (video on-demand and/or Internet-enabled units) are becoming integral to the patient and staff satisfaction standards in healthcare facilities. And as regulatory requirements continue to quickly evolve, it is inevitable that these on-demand education systems will become a standard feature of hospitals instead of a value add to the patient experience. The fact that these types of technological improvements already improve efficiency of healthcare facility personnel will likely be enough to encourage the quick acceptance of these improvements even without regulatory obligation.

As these new technologies are introduced into healthcare environments, healthcare professionals must continue to figure out new ways to use said technologies to assist with day-to-day tasks, such using technology to assist with the discussion of medical procedure results, including, but not limited to, X-rays, EKGs, labs, etc. As healthcare facilities have become more digitized, so has the form of the various medical procedure results. This is convenient in that a healthcare professional may quickly access results so long as they have a computing device that has access to the Electronic Health Record containing the desired information, but it also can prevent emotional interaction with the patient that may cause the healthcare professional to come off as cold. Reducing the amount of information visually available to the patient may also reduce the patient's understanding about a diagnosis and how said diagnosis may be corrected. For instance, a healthcare professional looking at a screen while a patient watches said healthcare professional look at said screen does nothing to assist a patient in understanding their condition. Further, smaller screens have been shown to reduce neural activity and attention, meaning that simply allowing patients to view information about their condition on a mobile device may have little impact on their understanding.

The increasingly digital healthcare industry has also resulted in additional security/safety issues as well. The aforementioned regulatory requirements are typically very strict when it comes to the dissemination of the contents of a patient's electronic health record (EHR). And though healthcare professionals are often careful with a patient's health records, mistakes cause distress to a patient unfortunately do happen. Whether the mistake is a result of mistaken identity of the patient, mistakenly selecting a different patient's health records in the EHR besides the patient intended, or something else, these mistakes are preventable. And preventing these mistakes could further increase patients' overall satisfaction while also further increasing the efficiency of healthcare professionals.

Accordingly, there is a need in the art for a system and method that may allow a healthcare professional to securely and quickly access data of an EHR as well as assist the healthcare professional present information of a patient's EHR to the patient in a way that increases said patient's understanding of their health.

SUMMARY

A system and method for quick, secure access to an electronic health record and assisting with the presentation of information to a patient is provided. Generally, the system and methods of the present disclosure are designed to enhance communication between a patient and the patient's healthcare provider. More specifically, the system and method are designed to more securely store information within an electronic health record while simultaneously increasing the ease in which a healthcare provider can share information with patients. The system generally comprises a first computing device having a first user interface, camera operably connected to said first computing device, access computing device having an access user interface, processor operably connected to said first computing device and said access computing device, display operably connected to said processor, and non-transitory computer-readable medium coupled to said processor and having instructions stored thereon. In one preferred embodiment, a database may be operably connected to the processor and the various data of the system may be stored therein, including, but not limited to, user data, patient data, and image data. In some preferred embodiments, a display having a display user interface and operably connected to the first computing device and a second computing device may comprise a plurality of display windows configured to display image data therein, wherein a control board of the display may be configured to receive said image data. In yet another preferred embodiment, a wireless communication interface may allow the processors of the system to receive and transmit image data therebetween.

A user preferably accesses the various data of the system by inputting commands within one of the carious user interfaces of the system. A user preferably may access patient data by using a first user interface of a first computing device to login to a user profile having permissions that allows said user to access patient data of the system, wherein said data is preferably related to a particular patient in an electronic health record (EHR). After logging into their user profile via the first user interface, the first user interface may require the user to use a camera of the first computing device to scan a predefined pattern of an access computing device, wherein the access computing device has access to the electronic health record storing said patient's patient data. Once scanned and confirmed, the first user interface may transmit a computer readable signal to the access computing device, wherein said computer readable signal may contain the user's login credentials (including the user's permission levels). This may allow the user to access a command line of the access user interface so that the user may access a patient's patient data stored within the system.

The system may also comprise a secondary security device, such as a biometric scanner, camera configured to collect image data for facial recognition, or bracelet having a unique identifier. In one preferred embodiment, the secondary security device may be operably connected to the access computing device and/or display in a way such that it is in direct communication with the access computing device and/or display and no other computing device and/or display. This may serve as an additional precaution to prevent the unintentional sharing of legally protected health records of a patient. In some preferred embodiments, the system may capture an identifying address of any computing device connected thereto via passive or active scanning. Other types of data that may be capture and saved by the system includes, but is not limited to, login time, login date, geolocation data, image data, or any combination thereof.

Some preferred embodiments of the display may comprise a control board having at least one circuit and microchip. The control board may control the plurality of display windows of the display user interface and the image data displayed therein. The microchip of the control board comprises a microprocessor and memory. In another preferred embodiment, the microchip may further comprise a wireless communication interface in the form of an antenna. The microprocessor may receive image data from at least one of a first computing device and second computing device via the wireless communication interface, wherein the image data comprises video data. Some preferred embodiments of image data may also include an audio data component. The control board may manipulate the image data and/or plurality of display windows based on commands received from an input device. In one preferred embodiment, the display user interface may also comprise a control window, which may allow a user to control the layout of the display user interface. For instance, a user may choose to layout that separates the display user interface of four separate display windows. Alternatively, an input device having a plurality of layouts thereon may be used to manipulate the layout of the display user interface.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other systems for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For instance, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises", and grammatical equivalents thereof are used herein to mean that other components, steps, etc. are optionally present. For instance, a system "comprising" components A, B, and C can contain only components A, B, and C, or can contain not only components A, B, and C, but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility). As will be evident from the disclosure provided below, the present invention satisfies the need for a system and method capable of seamlessly integrating controls into a video feed which allows the user to choose two or more media sources to combine.

Figure 1:
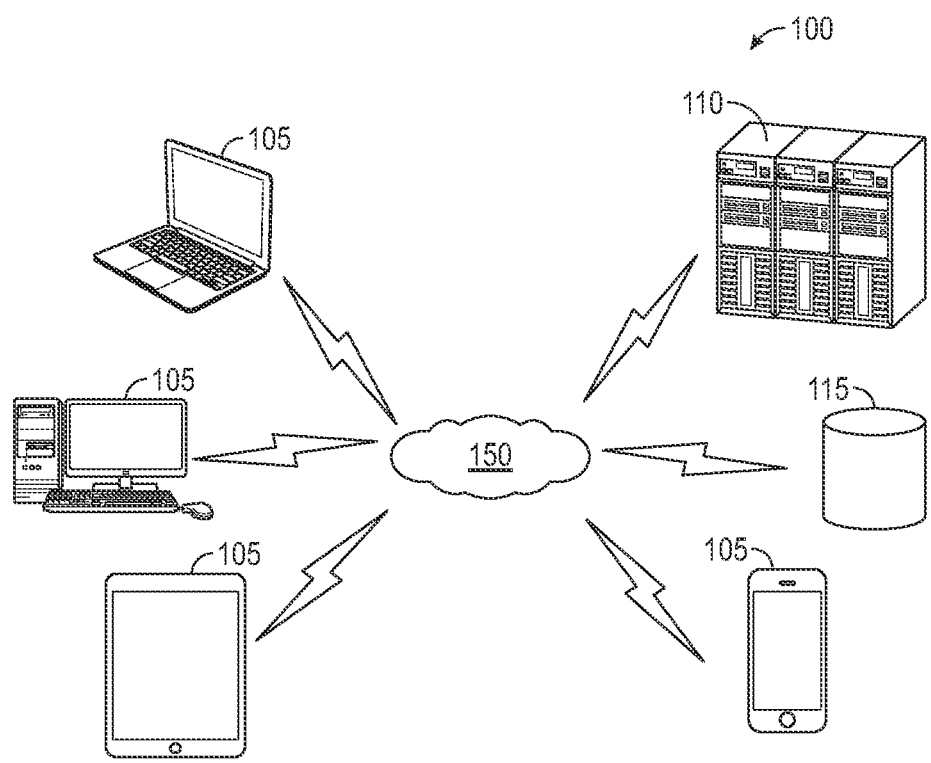
FIG. 1 illustrates a system embodying features consistent with the principles of the present disclosure.

FIG. 1 depicts an exemplary environment 100 of the system 400 consisting of clients 105 connected to a server 110 and/or database 115 via a network 150. Clients 105 are devices of users 405 that may be used to access servers 110 and/or databases 115 through a network 150. A network 150 may comprise of one or more networks of any kind, including, but not limited to, a local area network (LAN), a wide area network (WAN), metropolitan area networks (MAN), a telephone network, such as the Public Switched Telephone Network (PSTN), an intranet, the Internet, a memory device, another type of network, or a combination of networks. In a preferred embodiment, computing entities 200 may act as clients 105 for a user 405. For instance, a client 105 may include a personal computer, a wireless telephone, a streaming device, a "smart" television, a personal digital assistant (PDA), a laptop, a smart phone, a tablet computer, or another type of computation or communication interface 280. Servers 110 may include devices that access, fetch, aggregate, process, search, provide, and/or maintain documents. Although FIG. 1 depicts a preferred embodiment of an environment 100 for the system 400, in other implementations, the environment 100 may contain fewer components, different components, differently arranged components, and/or additional components than those depicted in FIG. 1. Alternatively, or additionally, one or more components of the environment 100 may perform one or more other tasks described as being performed by one or more other components of the environment 100.

As depicted in FIG. 1, one embodiment of the system 400 may comprise a server 110.

Although shown as a single server 110 in FIG. 1, a server 110 may, in some implementations, be implemented as multiple devices interlinked together via the network 150, wherein the devices may be distributed over a large geographic area and performing different functions or similar functions. For instance, two or more servers 110 may be implemented to work as a single server 110 performing the same tasks. Alternatively, one server 110 may perform the functions of multiple servers 110. For instance, a single server 110 may perform the tasks of a web server and an indexing server. Additionally, it is understood that multiple servers 110 may be used to operably connect the processor 220 to the database 115 and/or other content repositories. The processor 220 may be operably connected to the server 110 via wired or wireless connection. Types of servers 110 that may be used by the system 400 include, but are not limited to, search servers, document indexing servers, and web servers, or any combination thereof.

Search servers may include one or more computing entities 200 designed to implement a search engine, such as a documents/records search engine, general webpage search engine, etc. Search servers may, for instance, include one or more web servers designed to receive search queries and/or inputs from users 405, search one or more databases 115 in response to the search queries and/or inputs, and provide documents or information, relevant to the search queries and/or inputs, to users 405. In some implementations, search servers may include a web search server that may provide webpages to users 405, wherein a provided webpage may include a reference to a web server at which the desired information and/or links are located. The references to the web server at which the desired information is located may be included in a frame and/or text box, or as a link to the desired information/document. Document indexing servers may include one or more devices designed to index documents available through networks 150. Document indexing servers may access other servers 110, such as web servers that host content, to index the content. In some implementations, document indexing servers may index documents/records stored by other servers 110 connected to the network 150. Document indexing servers may, for instance, store and index content, information, and documents relating to user accounts and user-generated content. Web servers may include servers 110 that provide webpages to clients 105. For instance, the webpages may be HTML-based webpages. A web server may host one or more websites. As used herein, a website may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

As used herein, a database 115 refers to a set of related data and the way it is organized. Access to this data is usually provided by a database management system (DBMS) consisting of an integrated set of computer software that allows users 405 to interact with one or more databases 115 and provides access to all of the data contained in the database 115. The DBMS provides various functions that allow entry, storage and retrieval of large quantities of information and provides ways to manage how that information is organized. Because of the close relationship between the database 115 and the DBMS, as used herein, the term database 115 refers to both a database 115 and DBMS.

Figure 2:
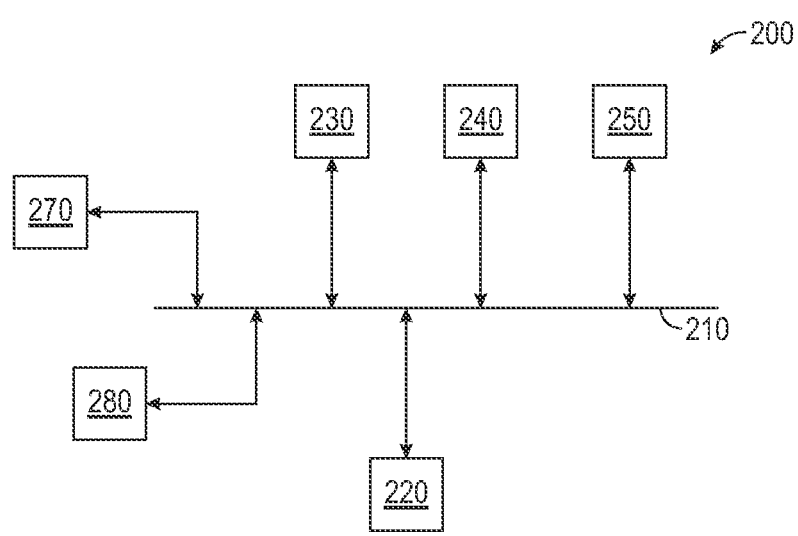
FIG. 2 illustrates a system embodying features consistent with the principles of the present disclosure.

FIG. 2 is an exemplary diagram of a client 105, server 110, and/or or database 115 (hereinafter collectively referred to as "computing entity 200"), which may correspond to one or more of the clients 105, servers 110, and databases 115 according to an implementation consistent with the principles of the invention as described herein. The computing entity 200 may comprise a bus 210, a processor 220, memory 304, a storage device 250, a peripheral device 270, and a communication interface 280 (such as wired or wireless communication device). The bus 210 may be defined as one or more conductors that permit communication among the components of the computing entity 200. The processor 220 may be defined as logic circuitry that responds to and processes the basic instructions that drive the computing entity 200. Memory 304 may be defined as the integrated circuitry that stores information for immediate use in a computing entity 200. A peripheral device 270 may be defined as any hardware used by a user 405 and/or the computing entity 200 to facilitate communicate between the two. A storage device 250 may be defined as a device used to provide mass storage to a computing entity 200. A communication interface 280 may be defined as any transceiver-like device that enables the computing entity 200 to communicate with other devices and/or computing entities 200.

The bus 210 may comprise a high-speed interface 308 and/or a low-speed interface 312 that connects the various components together in a way such they may communicate with one another. A high-speed interface 308 manages bandwidth-intensive operations for computing device 300, while a low-speed interface 312 manages lower bandwidth-intensive operations. In some preferred embodiments, the high-speed interface 308 of a bus 210 may be coupled to the memory 304, display 316, and to high-speed expansion ports 310, which may accept various expansion cards such as a graphics processing unit (GPU). In other preferred embodiments, the low-speed interface 312 of a bus 210 may be coupled to a storage device 250 and low-speed expansion ports 314. The low-speed expansion ports 314 may include various communication ports, such as USB, Bluetooth, Ethernet, wireless Ethernet, etc. Additionally, the low-speed expansion ports 314 may be coupled to one or more peripheral devices 270, such as a keyboard, pointing device, scanner, and/or a networking device, wherein the low-speed expansion ports 314 facilitate the transfer of input data from the peripheral devices 270 to the processor 220 via the low-speed interface 312.

The processor 220 may comprise any type of conventional processor or microprocessor that interprets and executes computer readable instructions. The processor 220 is configured to perform the operations disclosed herein based on instructions stored within the system 400. The processor 220 may process instructions for execution within the computing entity 200, including instructions stored in memory 304 or on a storage device 250, to display graphical information for a graphical user interface (GUI) on an external peripheral device 270, such as a display 316. The processor 220 may provide for coordination of the other components of a computing entity 200, such as control of user interfaces 411A, 411B, 511, 711, applications run by a computing entity 200, and wireless communication by a communication interface 280 of the computing entity 200. The processor 220 may be any processor or microprocessor suitable for executing instructions. In some embodiments, the processor 220 may have a memory device therein or coupled thereto suitable for storing the data, content, or other information or material disclosed herein. In some instances, the processor 220 may be a component of a larger computing entity 200. A computing entity 200 that may house the processor 220 therein may include, but are not limited to, laptops, desktops, workstations, personal digital assistants, servers 110, mainframes, cellular telephones, tablet computers, smart televisions, streaming devices, or any other similar device. Accordingly, the inventive subject matter disclosed herein, in full or in part, may be implemented or utilized in devices including, but are not limited to, laptops, desktops, workstations, personal digital assistants, servers 110, mainframes, cellular telephones, tablet computers, smart televisions, streaming devices, or any other similar device.

Memory 304 stores information within the computing device 300. In some preferred embodiments, memory 304 may include one or more volatile memory units. In another preferred embodiment, memory 304 may include one or more non-volatile memory units. Memory 304 may also include another form of computer-readable medium, such as a magnetic, solid state, or optical disk. For instance, a portion of a magnetic hard drive may be partitioned as a dynamic scratch space to allow for temporary storage of information that may be used by the processor 220 when faster types of memory, such as random-access memory (RAM), are in high demand. A computer-readable medium may refer to a non-transitory computer-readable memory device. A memory device may refer to storage space within a single storage device 250 or spread across multiple storage devices 250. The memory 304 may comprise main memory 230 and/or read only memory (ROM) 240. In a preferred embodiment, the main memory 230 may comprise RAM or another type of dynamic storage device 250 that stores information and instructions for execution by the processor 220. ROM 240 may comprise a conventional ROM device or another type of static storage device 250 that stores static information and instructions for use by processor 220. The storage device 250 may comprise a magnetic and/or optical recording medium and its corresponding drive.

As mentioned earlier, a peripheral device 270 is a device that facilitates communication between a user 405 and the processor 220. The peripheral device 270 may include, but is not limited to, an input device and/or an output device. As used herein, an input device may be defined as a device that allows a user 405 to input data and instructions that is then converted into a pattern of electrical signals in binary code that are comprehensible to a computing entity 200. An input device of the peripheral device 270 may include one or more conventional devices that permit a user 405 to input information into the computing entity 200, such as a controller, scanner, phone, camera, scanning device, keyboard, a mouse, a pen, voice recognition and/or biometric mechanisms, etc. As used herein, an output device may be defined as a device that translates the electronic signals received from a computing entity 200 into a form intelligible to the user 405. An output device of the peripheral device 270 may include one or more conventional devices that output information to a user 405, including a display 316, a printer, a speaker, an alarm, a projector, etc. Additionally, storage devices 250, such as CD-ROM drives, and other computing entities 200 may act as a peripheral device 270 that may act independently from the operably connected computing entity 200. For instance, a streaming device may transfer data to a smartphone, wherein the smartphone may use that data in a manner separate from the streaming device.

The storage device 250 is capable of providing the computing entity 200 mass storage. In some embodiments, the storage device 250 may comprise a computer-readable medium such as the memory 304, storage device 250, or memory 304 on the processor 220. A computer-readable medium may be defined as one or more physical or logical memory devices and/or carrier waves. Devices that may act as a computer readable medium include, but are not limited to, a hard disk device, optical disk device, tape device, flash memory or other similar solid-state memory device, or an array of devices, including devices in a storage area network or other configurations. Examples of computer-readable mediums include, but are not limited to, magnetic media such as hard disks, floppy disks, and magnetic tape; optical media such as CD ROM discs and DVDs; magneto-optical media such as optical discs; and hardware devices that are specially configured to store and perform programming instructions, such as ROM 240, RAM, flash memory, and the like.

In an embodiment, a computer program may be tangibly embodied in the storage device 250. The computer program may contain instructions that, when executed by the processor 220, performs one or more steps that comprise a method, such as those methods described herein. The instructions within a computer program may be carried to the processor 220 via the bus 210. Alternatively, the computer program may be carried to a computer-readable medium, wherein the information may then be accessed from the computer-readable medium by the processor 220 via the bus 210 as needed. In a preferred embodiment, the software instructions may be read into memory 304 from another computer-readable medium, such as data storage device 250, or from another device via the communication interface 280. Alternatively, hardwired circuitry may be used in place of or in combination with software instructions to implement processes consistent with the principles as described herein. Thus, implementations consistent with the invention as described herein are not limited to any specific combination of hardware circuitry and software.

Figure 3:
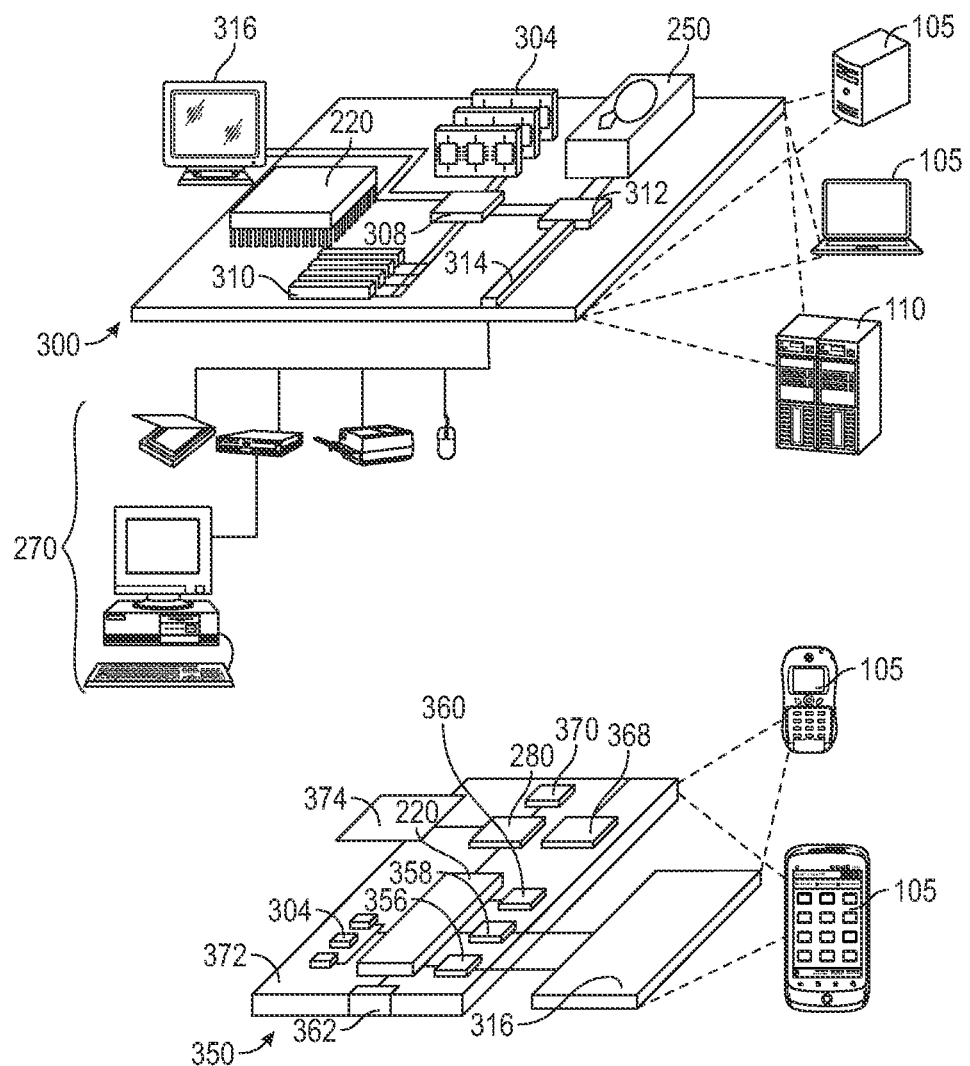
FIG. 3 illustrates a system embodying features consistent with the principles of the present disclosure.

FIG. 3 depicts exemplary computing entities 200 in the form of a computing device 300 and mobile computing device 350, which may be used to carry out the various embodiments of the invention as described herein. A computing device 300 is intended to represent various forms of digital computers, such as laptops, desktops, workstations, servers 110, databases 115, mainframes, and other appropriate computers. A mobile computing device 350 is intended to represent various forms of mobile devices, such as scanners, scanning devices, personal digital assistants, cellular telephones, smart phones, tablet computers, and other similar devices. The various components depicted in FIG. 3, as well as their connections, relationships, and functions are meant to be examples only, and are not meant to limit the implementations of the invention as described herein. The computing device 300 may be implemented in a number of different forms, as shown in FIGS. 1 and 3. For instance, a computing device 300 may be implemented as a server 110 or in a group of servers 110. Computing devices 300 may also be implemented as part of a rack server system. In addition, a computing device 300 may be implemented as a personal computer, such as a desktop computer or laptop computer. Alternatively, components from a computing device 300 may be combined with other components in a mobile device, thus creating a mobile computing device 350. Each mobile computing device 350 may contain one or more computing devices 300 and mobile devices, and an entire system may be made up of multiple computing devices 300 and mobile devices communicating with each other as depicted by the mobile computing device 350 in FIG. 3. The computing entities 200 consistent with the principles of the invention as disclosed herein may perform certain receiving, communicating, generating, output providing, correlating, and storing operations as needed to perform the various methods as described in greater detail below.

In the embodiment depicted in FIG. 3, a computing device 300 may include a processor 220, memory 304 a storage device 250, high-speed expansion ports 310, low-speed expansion ports 314, and bus 210 operably connecting the processor 220, memory 304, storage device 250, high-speed expansion ports 310, and low-speed expansion ports 314. In one preferred embodiment, the bus 210 may comprise a high-speed interface 308 connecting the processor 220 to the memory 304 and high-speed expansion ports 310 as well as a low-speed interface 312 connecting to the low-speed expansion ports 314 and the storage device 250. Because each of the components are interconnected using the bus 210, they may be mounted on a common motherboard as depicted in FIG. 3 or in other manners as appropriate. The processor 220 may process instructions for execution within the computing device 300, including instructions stored in memory 304 or on the storage device 250. Processing these instructions may cause the computing device 300 to display graphical information for a GUI on an output device, such as a display 316 coupled to the high-speed interface 308. In other implementations, multiple processors and/or multiple buses may be used, as appropriate, along with multiple memory units and/or multiple types of memory. Additionally, multiple computing devices may be connected, wherein each device provides portions of the necessary operations.

A mobile computing device 350 may include a processor 220, memory 304 a peripheral device 270 (such as a display 316, a communication interface 280, and a transceiver 368, among other components). A mobile computing device 350 may also be provided with a storage device 250, such as a micro-drive or other previously mentioned storage device 250, to provide additional storage. Preferably, each of the components of the mobile computing device 350 are interconnected using a bus 210, which may allow several of the components of the mobile computing device 350 to be mounted on a common motherboard as depicted in FIG. 3 or in other manners as appropriate. In some implementations, a computer program may be tangibly embodied in an information carrier. The computer program may contain instructions that, when executed by the processor 220, perform one or more methods, such as those described herein. The information carrier is preferably a computer-readable medium, such as memory, expansion memory 374, or memory 304 on the processor 220 such as ROM 240, that may be received via the transceiver or external interface 362. The mobile computing device 350 may be implemented in a number of different forms, as shown in FIG. 3. For instance, a mobile computing device 350 may be implemented as a cellular telephone, part of a smart phone, personal digital assistant, or other similar mobile device.

The processor 220 may execute instructions within the mobile computing device 350, including instructions stored in the memory 304 and/or storage device 250. The processor 220 may be implemented as a chipset of chips that may include separate and multiple analog and/or digital processors. The processor 220 may provide for coordination of the other components of the mobile computing device 350, such as control of the user interfaces 411A, 411B, 511, 711, applications run by the mobile computing device 350, and wireless communication by the mobile computing device 350. The processor 220 of the mobile computing device 350 may communicate with a user 405 through the control interface 358 coupled to a peripheral device 270 and the display interface 356 coupled to a display 316. The display 316 of the mobile computing device 350 may include, but is not limited to, Liquid Crystal Display (LCD), Light Emitting Diode (LED) display, Organic Light Emitting Diode (OLED) display, and Plasma Display Panel (PDP), holographic displays, augmented reality displays, virtual reality displays, or any combination thereof. The display interface 356 may include appropriate circuitry for causing the display 316 to present graphical and other information to a user 405. The control interface 358 may receive commands from a user 405 via a peripheral device 270 and convert the commands into a computer readable signal for the processor 220. In addition, an external interface 362 may be provided in communication with processor 220, which may enable near area communication of the mobile computing device 350 with other devices. The external interface 362 may provide for wired communications in some implementations or wireless communication in other implementations. In a preferred embodiment, multiple interfaces may be used in a single mobile computing device 350 as is depicted in FIG. 3.

Memory 304 stores information within the mobile computing device 350. Devices that may act as memory 304 for the mobile computing device 350 include, but are not limited to computer-readable media, volatile memory, and non-volatile memory. Expansion memory 374 may also be provided and connected to the mobile computing device 350 through an expansion interface 372, which may include a Single In-Line Memory Module (SIM) card interface or micro secure digital (Micro-SD) card interface. Expansion memory 374 may include, but is not limited to, various types of flash memory and non-volatile random-access memory (NVRAM). Such expansion memory 374 may provide extra storage space for the mobile computing device 350. In addition, expansion memory 374 may store computer programs or other information that may be used by the mobile computing device 350. For instance, expansion memory 374 may have instructions stored thereon that, when carried out by the processor 220, cause the mobile computing device 350 perform the methods described herein. Further, expansion memory 374 may have secure information stored thereon; therefore, expansion memory 374 may be provided as a security module for a mobile computing device 350, wherein the security module may be programmed with instructions that permit secure use of a mobile computing device 350. In addition, expansion memory 374 having secure applications and secure information stored thereon may allow a user 405 to place identifying information on the expansion memory 374 via the mobile computing device 350 in a non-hackable manner.

A mobile computing device 350 may communicate wirelessly through the communication interface 280, which may include digital signal processing circuitry where necessary. The communication interface 280 may provide for communications under various modes or protocols, including, but not limited to, Global System Mobile Communication (GSM), Short Message Services (SMS), Enterprise Messaging System (EMS), Multimedia Messaging Service (MMS), Code Division Multiple Access (CDMA), Time Division Multiple Access (TDMA), Personal Digital Cellular (PDC), Wideband Code Division Multiple Access (WCDMA), IMT Multi-Carrier (CDMAX 0), and General Packet Radio Service (GPRS), or any combination thereof. Such communication may occur, for example, through a transceiver 368. Short-range communication may occur, such as using a Bluetooth, WIFI, or other such transceiver 368. In addition, a Global Positioning System (GPS) receiver module 370 may provide additional navigation- and location-related wireless data to the mobile computing device 350, which may be used as appropriate by applications running on the mobile computing device 350. Alternatively, the mobile computing device 350 may communicate audibly using an audio codec 360, which may receive spoken information from a user 405 and covert the received spoken information into a digital form that may be processed by the processor 220. The audio codec 360 may likewise generate audible sound for a user 405, such as through a speaker, e.g., in a handset of mobile computing device 350. Such sound may include sound from voice telephone calls, recorded sound such as voice messages, music files, etc. Sound may also include sound generated by applications operating on the mobile computing device 350.

The system 400 may also comprise a power supply. The power supply may be any source of power that provides the system 400 with power. In an embodiment, the power supply may be a stationary power outlet. The system 400 may comprise of multiple power supplies that may provide power to the system 400 in different circumstances. For instance, the system 400 may be directly plugged into a stationary power outlet, which may provide power to the system 400 so long as it remains in one place. However, the system 400 may also be connected to a backup battery so that the system 400 may receive power even when the power supply is not connected to a stationary power outlet or if the stationary power outlet ceases to provide power to the computing entity 200.

Figure 4:
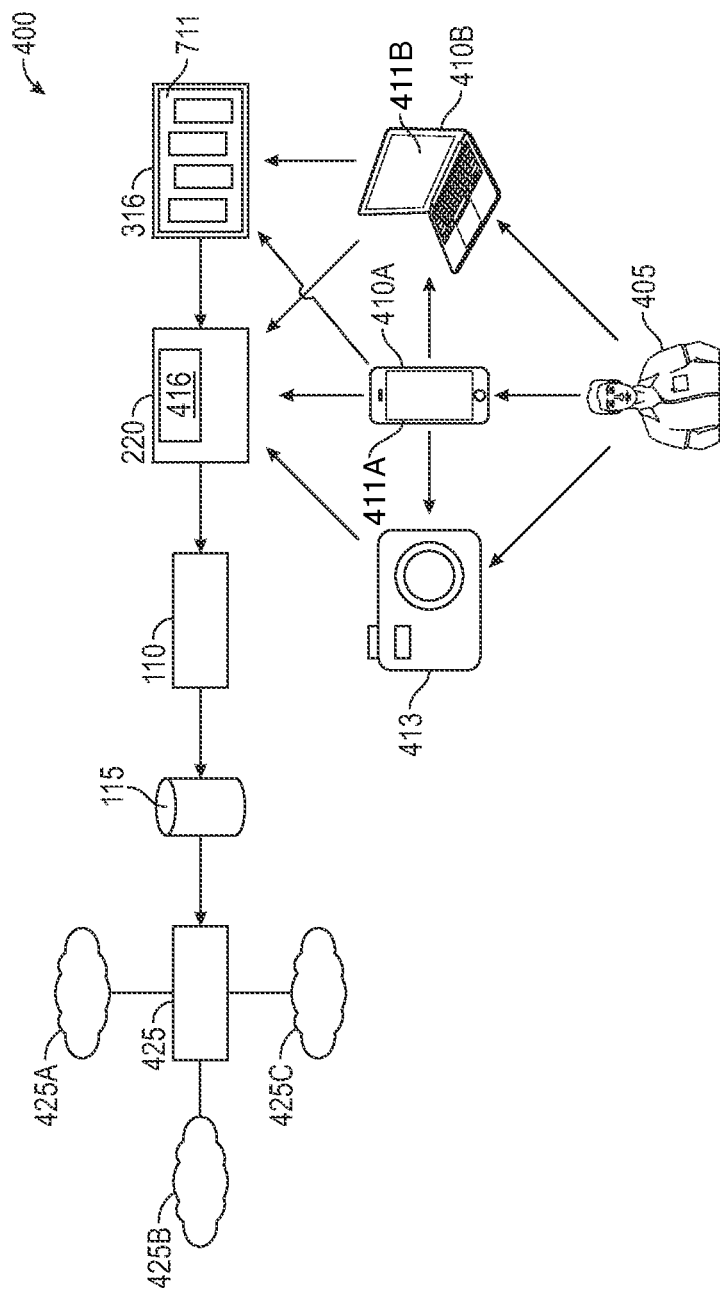
FIG. 4 illustrates a system embodying features consistent with the principles of the present disclosure.
Figure 5:
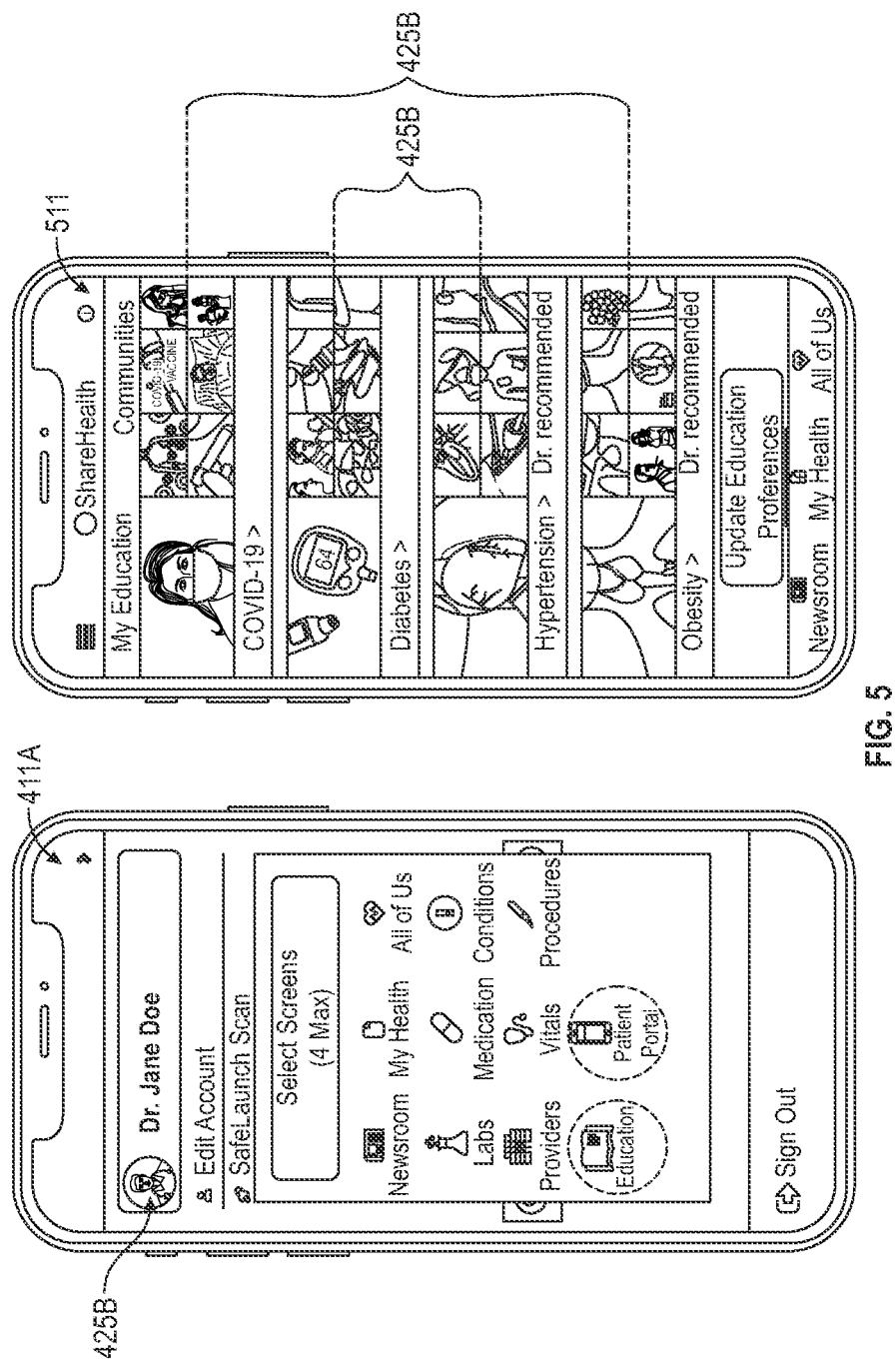
FIG. 5 illustrates a system embodying features consistent with the principles of the present disclosure.
Figure 6:
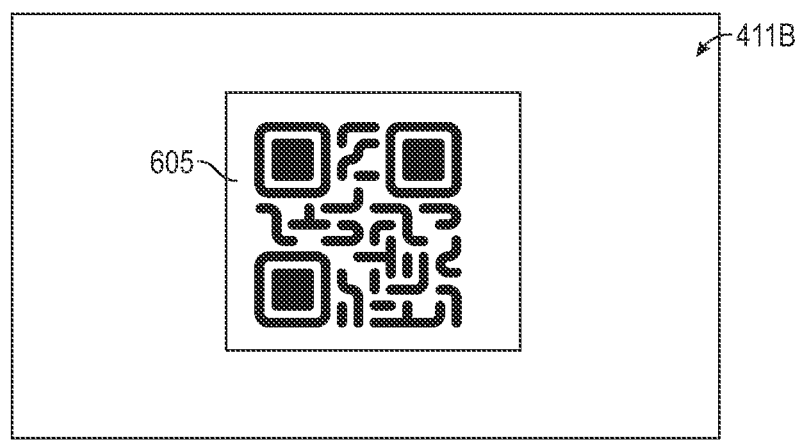
FIG. 6 illustrates a system embodying features consistent with the principles of the present disclosure.
Figure 7:
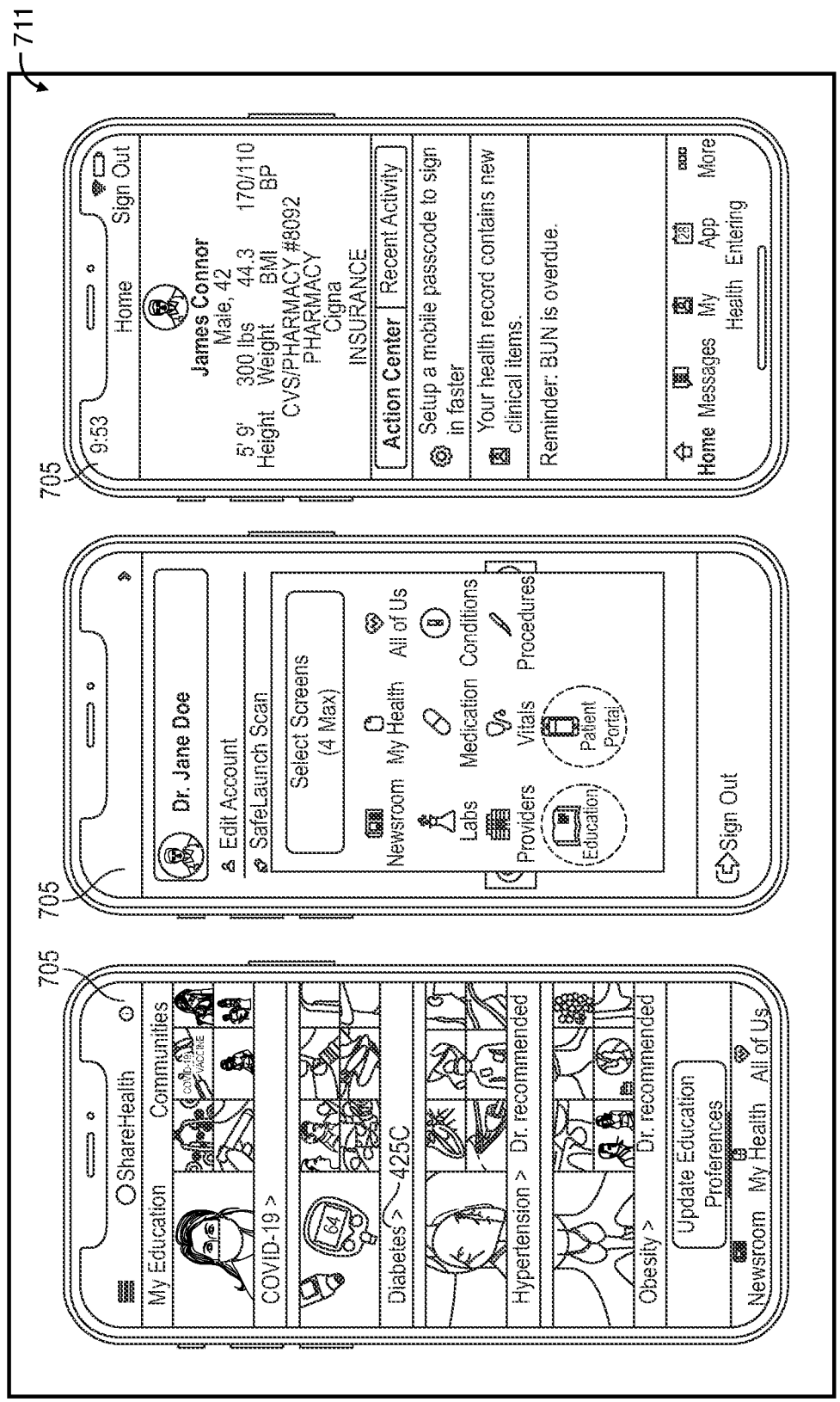
FIG. 7 illustrates a system embodying features consistent with the principles of the present disclosure.
Figure 8:
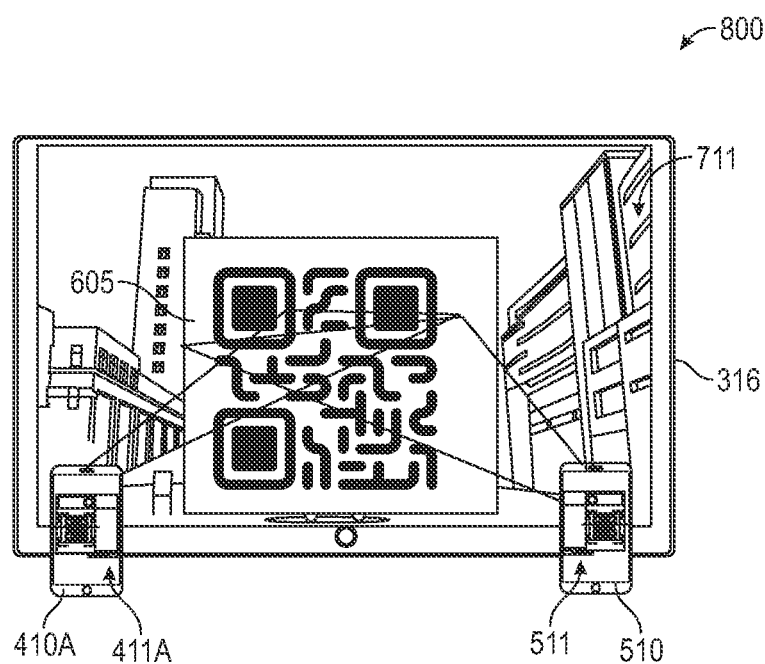
FIG. 8 illustrates an example environment in which a user may use the system and implement the techniques of the present disclosure.
Figure 9:
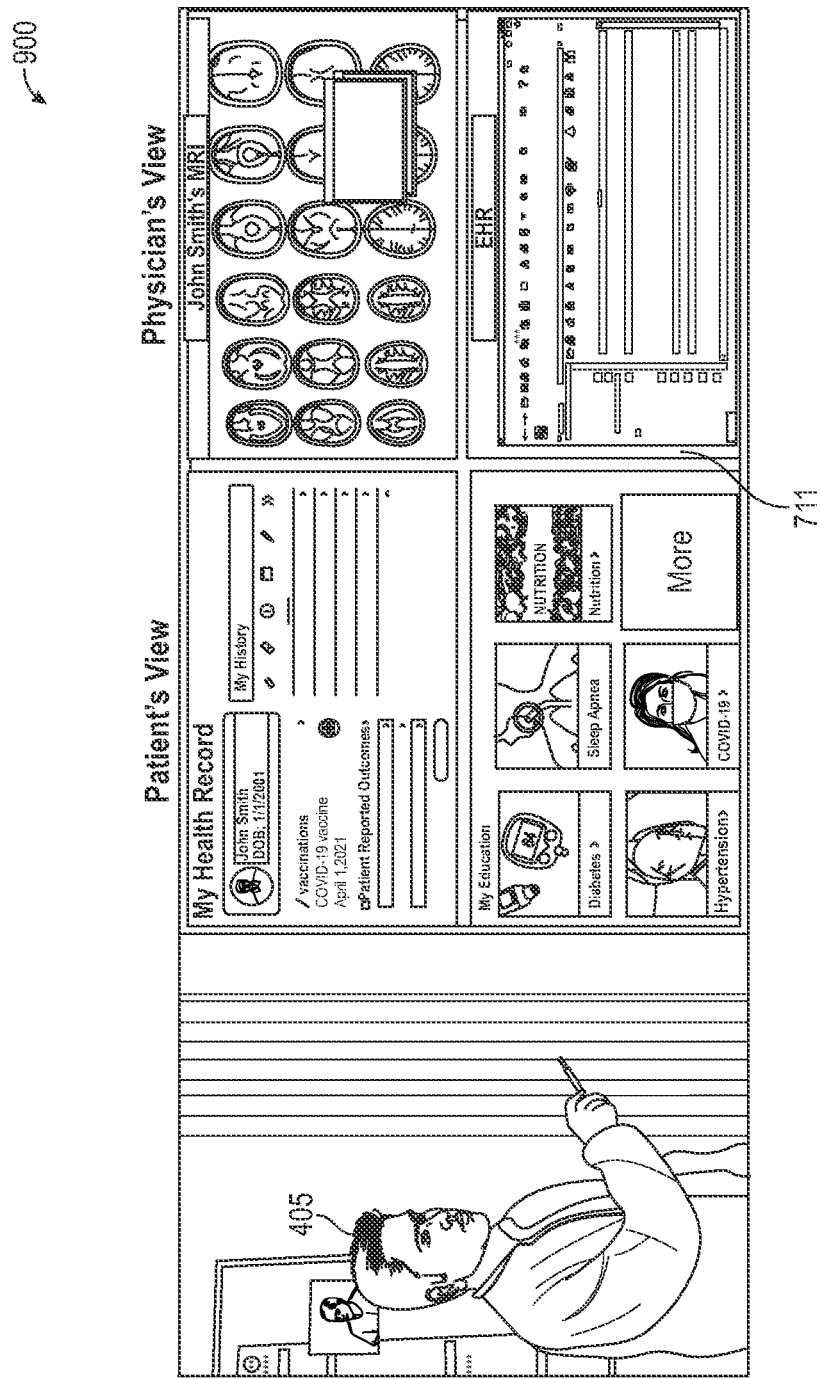
FIG. 9 illustrates an example environment in which a user may use the system and implement the techniques of the present disclosure.
Figure 10:
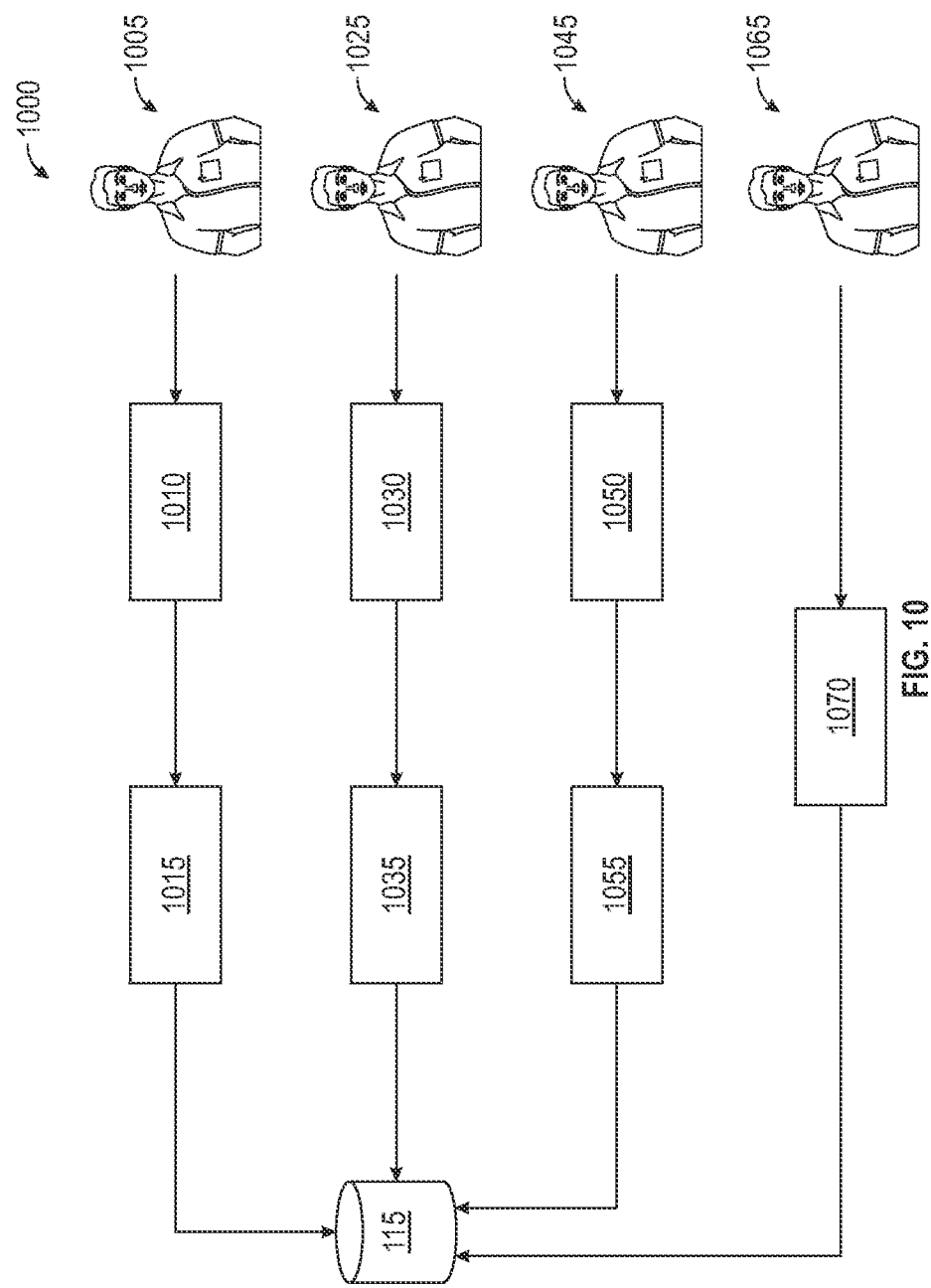
FIG. 10 is a diagram illustrating the manner in which individual access to data may be granted or limited based on user roles and administrator roles.
Figure 11:
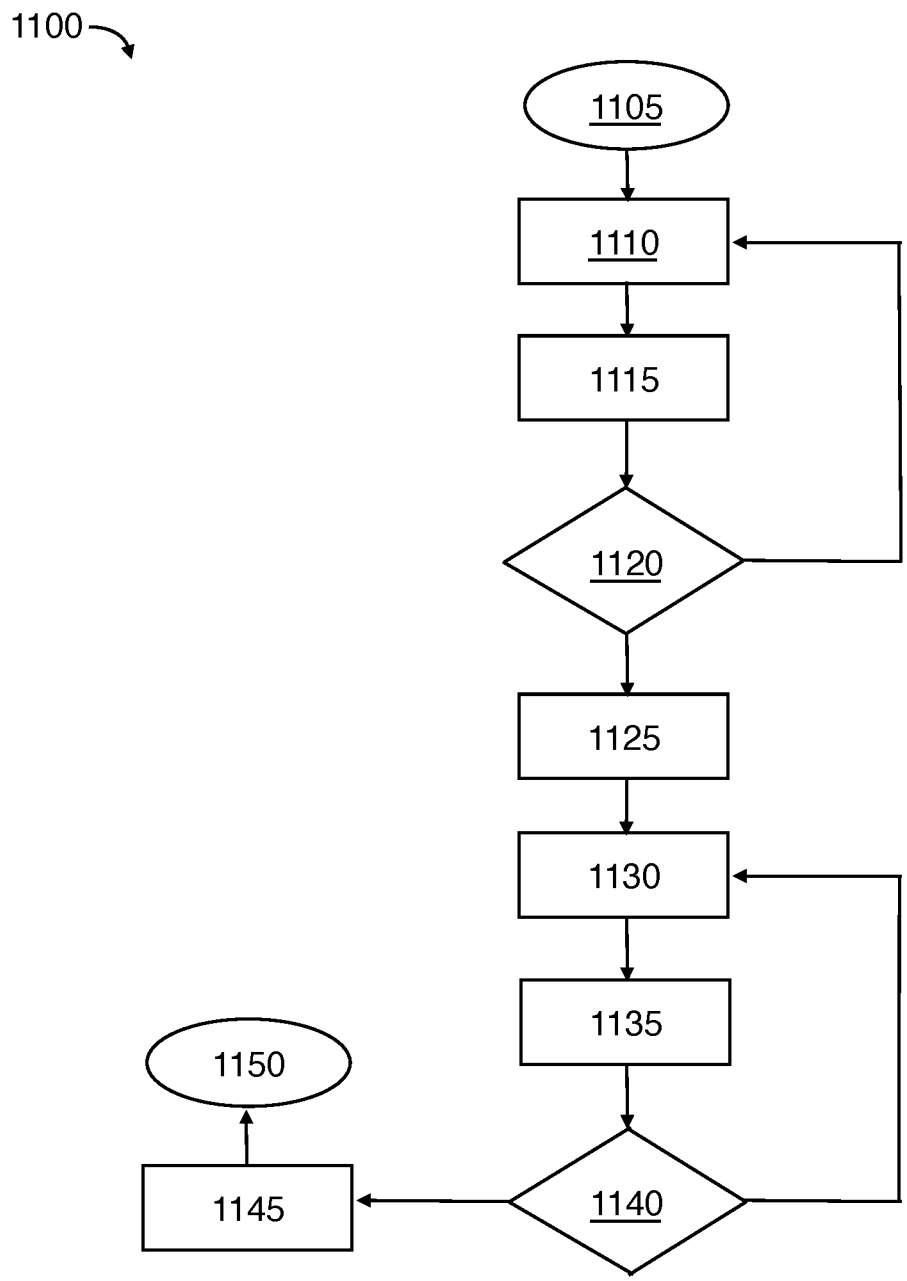
FIG. 11 is a flow chart illustrating certain method steps of a method embodying features consistent with the principles of the present disclosure.
Figure 12:
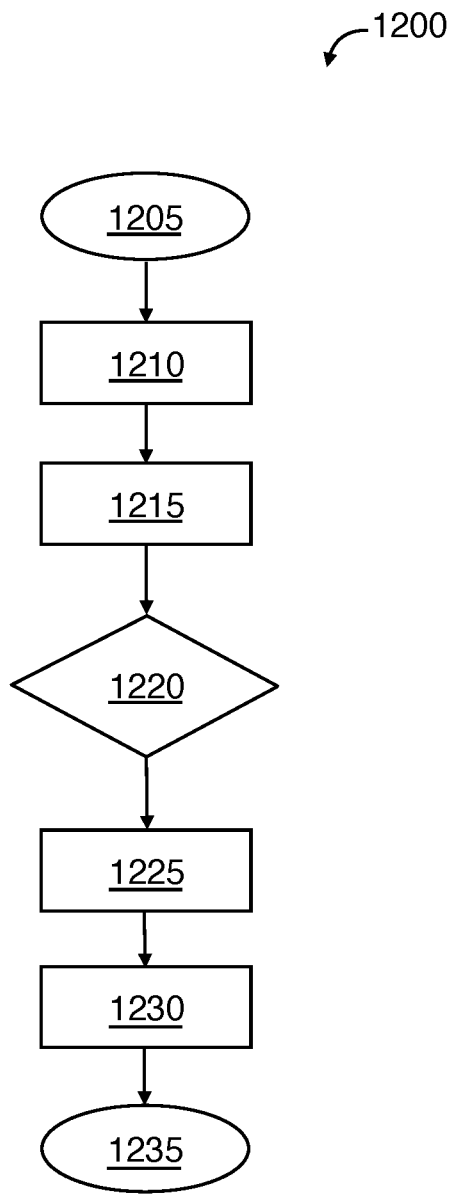
FIG. 12 is a flow chart illustrating certain method steps of a method embodying features consistent with the principles of the present disclosure.
Figure 13:
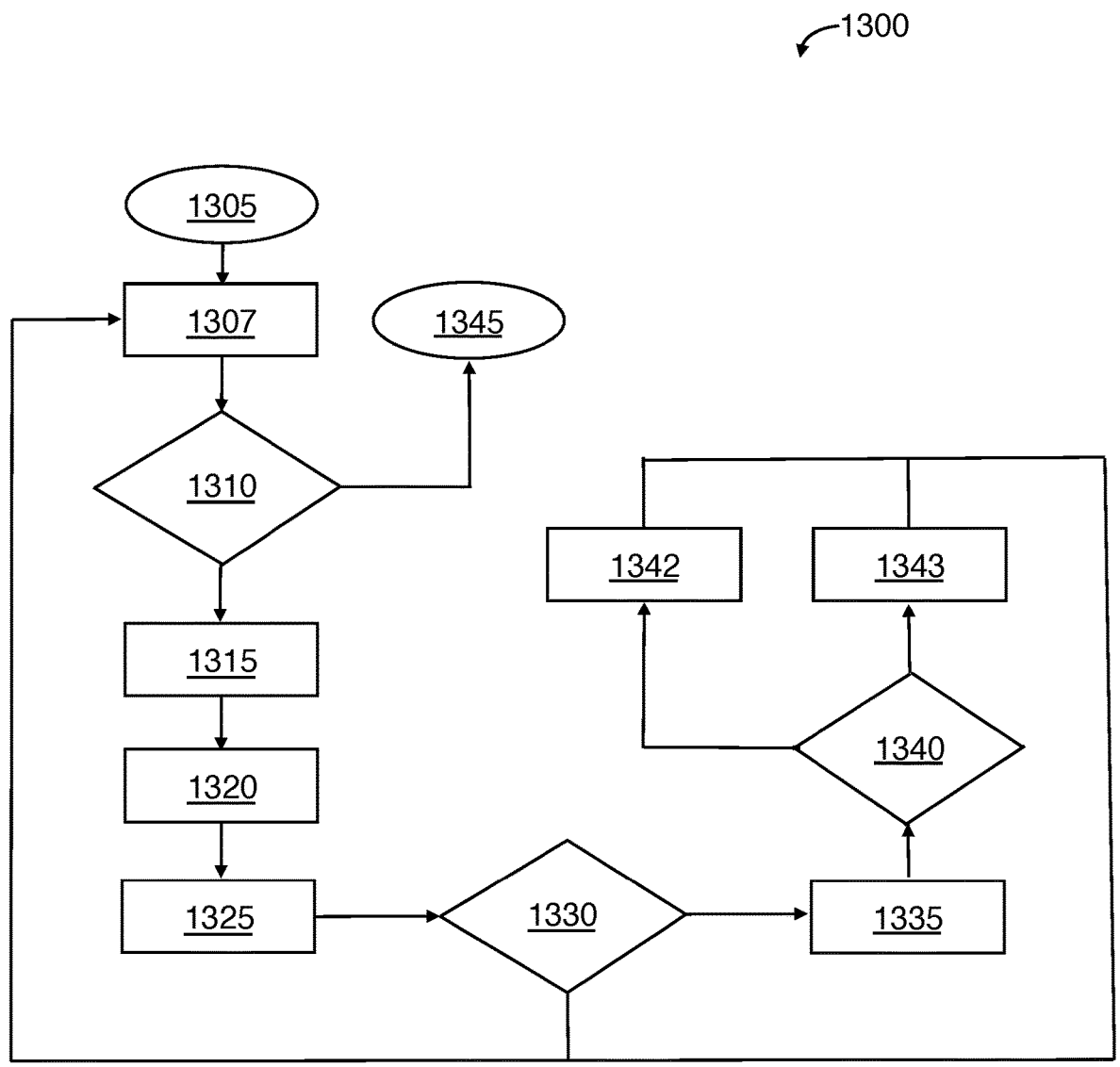
FIG. 13 is a flow chart illustrating certain method steps of a method embodying features consistent with the principles of the present disclosure.

FIGS. 4-13 illustrate embodiments of a system 400 and methods for securely displaying patient data 425B within a plurality of display windows 705 of a display user interface 711 of a display 316. FIG. 4 illustrates a preferred embodiment of the system 400 having a first computing device 410A and access computing device 410B in fluid communication with one another. FIG. 5 illustrates an example first user interface 411A of the first computing device 410A and a second user interface 511 of a second computing device 510, wherein a display 316 operably connected to said first computing device 410A and second computing device 510 may receive said first user interface 411A from said first computing device 410A and said second user interface 511 from said second computing device 510 in the form of image data 425C. FIG. 6 illustrates an example access user interface 411B of the access computing device 410B, wherein a display 316 operably connected to said access computing device 410B may present a predetermined pattern 605 containing login credentials of said access computing device 410B. FIG. 7 illustrates an example display user interface 711 of the display 316, wherein a control board operably connected to said display 316 may receive image data 425C from said first computing device 410A and said second computing device 510 and present it within said display user interface 711. FIGS. 8 and 9 illustrate environmental views 800, 900 of the system 400 being used by a user 405. FIG. 10 illustrates permission levels 1000 that may be utilized by the present system 400 for controlling access to user content 1015, 1035, 1055 such as user data 425A, patient data 425B, image data 425C. FIGS. 11-13 illustrate methods 1100, 1200, 1300 that may be carried out by the system 400. It is understood that the various method steps associated with the methods 1100, 1200, 1300, of the present disclosure may be carried out as operations by the system 400 shown in FIG. 4.

The system 400 generally comprises a first computing device 410A having a first user interface 411A, camera 413 operably connected to said first computing device 410A, access computing device 410B having an access user interface 411B, processor 220 operably connected to said first computing device 410A and said access computing device 410B, display 316 operably connected to said processor 220, and non-transitory computer-readable medium 416 coupled to said processor 220 and having instructions stored thereon. In one preferred embodiment, a database 115 may be operably connected to the processor 220 and the various data of the system 400 may be stored therein, including, but not limited to, user data 425A, patient data 425B, and image data 425C. In some preferred embodiments, a display 316 having a display user interface 711 and operably connected to the first computing device 410A and a second computing device 510 may comprise a plurality of display windows 705 configured to display image data 425C therein, wherein a control board of the display 316 may be configured to receive said image data 425C. In yet another preferred embodiment, a wireless communication interface 280 may allow the processors 220 of the system 400 to receive and transmit image data 425C therebetween. Though computing devices are referred to as first computing device 110A, access computing device 110B, and second computing device 510, one with skill in the art will recognize instances in which said computing devices may be used interchangeably without departing from the inventive subject matter described herein.

A user 405 preferably accesses the various data of the system 400 by inputting commands within a user interface of a computing device that allows the user 405 to access to said data. In a preferred embodiment, as illustrated in FIGS. 8 and 9, a user 405 may access said patient data 425B by using a first user interface 411A of a first computing device 410A to login to a user profile 425 having permissions 1000 that allows said user 405 to access patient data 425B of the system 400, wherein said data is preferably related to a particular patient in an electronic health record (EHR). After logging into their user profile 425 via the first user interface 411A, the first user interface 411A may require the user 405 to use a camera 413 of the first computing device 410A to scan a predefined pattern 605 of an access computing device 410B, wherein the access computing device 410B has access to the electronic health record storing said patient's patient data 425B. Once scanned and confirmed, the first user interface 411A may transmit a computer readable signal to the access computing device 410B, wherein said computer readable signal may contain the user's 405 login credentials (including the user's 405 permission levels 1000). This may allow the user 405 to access a command line of the access user interface 411B so that the user 405 may access a patient's patient data 425B stored within the system 400.

In one preferred embodiment, the system 400 may further comprise a secondary security device, such as a biometric scanner, camera configured to collect image data for facial recognition, or bracelet having a unique identifier. In one preferred embodiment, the secondary security device may be operably connected to the access computing device 410B and/or display 316 in a way such that it is in direct communication with the access computing device 410B and/or display 316 and no other computing device and/or display 316. For instance, the secondary security device may be connected to a control board of the display 316 such that a healthcare professional and patient must biometrically scan their thumbprint and/or face prior to the display 316 activating. This may serve as an additional precaution to prevent the unintentional sharing of legally protected health records of a patient. The first computing device 410A, access computing device 410B, second computing device 510, server 110, database 115, display 316, and secondary security device may be connected via a wired or wireless connection. In a preferred embodiment, the first computing device 410A, access computing device 410B, second computing device 510, and display 316 are connected via a wireless connection, such as Bluetooth, whereas the secondary security device has a wired connection with the access computing device 410B and/or display 316.

In another preferred embodiment, the secondary security device may contain a transmitter containing a unique ID, which may be transmitted to an access computing device 410B and/or display 316 in the form of a computer readable signal before deciding whether or not to allow a user 405 to access the system 400. Unique IDs contained within the signal broadcast by the transmitter may include, but are not limited to, unique identifier codes, social security numbers, PINs, etc. For instance, a computer readable signal broadcast by a secondary security device in the form of a bracelet may contain information that will alert the system 400 that a particular user 405 is within a certain range of a particular computing device, which may cause the system 400 to activate said particular computing device if additional steps are taken. Alternatively, the system 400 may be configured to prevent activation of a display if a particular user 405 is within range. For instance, before conveying classified information to a group of military personnel, the system 400 may check to determine if a user 405 is within range that doesn't have permissions to view said classified information. If a user 405 without an appropriate permission level 1000 is within range of the display 316, the system 400 will not activate.

Types of devices that may act as the transmitter include, but are not limited, to near field communication (NFC), Bluetooth, infrared (IR), radio-frequency communication (RFC), radio-frequency identification (RFID), and ANT+, or any combination thereof. In an embodiment, transmitters may broadcast signals of more than one type. For instance, a transmitter comprising an IR transmitter and RFID transmitter may broadcast IR signals and RFID signals. Alternatively, a transmitter may broadcast signals of only one type of signal. For instance, ID badges may be fitted with transmitters that broadcast only NFC signals containing unique IDs that computing devices equipped with NFC receivers must receive before being activated by a user 405.

In yet another preferred embodiment, the secondary security device may comprise a predefined pattern 605 that a user 405 must scan before the system 400 will allow said user 405 to activate a particular computing device. For instance, a healthcare professional wanting to discuss medical test results with a patient may have to scan a predefined pattern 605 of a bracelet of a patient, which may then cause a display 316 operably connected to the healthcare professional's computing device and patient's computing device to activate. For instance, a healthcare professional wanting to access a particular access computing device 410B operably connected to the EHR may be required to scan a predefined pattern 605 of an ID badge using a scanning device of said particular access computing device 410B. Further, the system 400 may comprise a plurality of secondary security devices that may be used to protect users 405 of the system 400. For instance, the system 400 may use a combination of a biometric scanning device and a bracelet having a scannable predefined pattern 605 in addition to the methods of transmitting login credentials from a first computing device 410A to an access computing device 410B in the manners described herein. Therefore, one with skill in the art will recognize that a plurality of methods may be used to secure information of the system 400 without departing from the inventive subject matter described herein.

In some preferred embodiments, the system 400 may capture an identifying address of any computing device connected thereto. An identifying address may include, but is not limited to, basic service set identifier (BSSID), extended service set identifier (ESSID), service set identifier (SSID), and media access control (MAC) address, or any combination thereof. For instance, the system 400 may capture a MAC address of a computing device wirelessly connected to the system 400 via Bluetooth. The system 400 may capture identifying addresses by actively scanning or passively scanning for computing devices capable of wirelessly connecting to the system 400. In another preferred embodiment, computing devices may be configured to send a computer readable signal containing said identifying address. For instance, the first computing device 410A may be required to send an identifying address along with login credentials to the access computing device 410B via a computer readable signal prior to said access computing device 410B allowing a user 405 to access an EHR. In some preferred embodiments, login credentials and the identifying address may be saved by the system as log data, wherein said log data may allow the system 400 to keep a record on which users 405 access which computing devices and/or displays 316 of the system 400. Other types of data that may be saved by the system 400 as log data includes, but is not limited to, login time, login date, geolocation data, image data 425C, or any combination thereof.

In a preferred embodiment, the various data of the system 400 may be stored in user profiles 425. Types of data that may be stored within user profiles 425 of the system 400 include, but are not limited to, user data 425A, patient data 425B, and image data 425C. One preferred embodiment of the system 400 may comprise a database 115 operably connected to the processor 220. The database 115 may be configured to store user data 425A and patient data 425B within said user profiles 425. As used herein, user data 425A may be defined as personal information of a user 405 that helps the system 400 identify the user 405. Types of data that may be used by the system 400 as user data 425A includes, but is not limited to, a user's name, username, social security number, phone number, gender, age, or any combination thereof. As used herein, patient data 425B is data related to a patient's medical record, which may usually be found within an electronic health record. Types of data that may be used by the system 400 as patient data 425B includes, but is not limited to, encounter notes, lab/image reports, orders, medications, guidelines, assessments, interventions, pathological reports, or any combination thereof.

The database 115 may also be configured to store image data 425C of the system 400, and in some preferred embodiments, the same may act as a distributor of image data 425C to the plurality of display windows 705 of the display user interface 711 of a display 316. Alternatively, the processor 220 and/or database 115 may transmit image data 425C to a server 110, which may act as a distributor of image data 425C to the plurality of display windows 705 of the display user interface 711 of a display 316. Once the server 110 has distributed image data 425C to a first display user interface 711 of a first display 316, it may transmit a mirrored version of the first display user interface 711 to a second display user interface 711 of a second display 316. In some preferred embodiments, the server 110 may also transmit said mirrored version to the database 115 to be saved as image data 425C therein. In a preferred embodiment, a user profile 425 is related to a particular user 405. A user 405 is preferably associated with a particular user profile 425 based on a username. However, it is understood that a user 405 may be associated with a user profile 425 using a variety of methods without departing from the inventive subject matter herein.

As previously mentioned, some preferred embodiments of the display 316 may further comprise a control board. The control board comprises at least one circuit and microchip. In another preferred embodiment, the control board may further comprise a wireless communication interface 280, which may allow the control board to receive instructions from an input device controlled by a user 405. In a preferred embodiment, the control board may control the plurality of display windows 705 of the display user interface 711 and the image data 425C displayed therein. The microchip of the control board comprises a microprocessor and memory. In another preferred embodiment, the microchip may further comprise a wireless communication interface 280 in the form of an antenna 420. The microprocessor may be defined as a multipurpose, clock driven, register based, digital-integrated circuit which accepts binary data as input, processes it according to instructions stored in its memory, and provides results as output. In a preferred embodiment, the microprocessor may receive image data 425C from at least one of a first computing device 410A and second computing device 510 via the wireless communication interface 280, wherein the image data 425C comprises video data. Some preferred embodiments of image data 425C may also include an audio data component. In another preferred embodiment, the microprocessor may receive image data 425C from the communication interface 280 in the form of a live stream. For instance, image data 425C pertaining to a recording of a patient snoring during a sleep study may include both a video component and an audio component.

As mentioned previously, the system 400 may further comprise a plurality of user interfaces 411A, 411B, 511, 711. A user interface 411 may be defined as a space where interactions between a user 405 and the system 400 may take place. In an embodiment, the interactions may take place in a way such that a user 405 may control the operations of the system 400. A user interface may include, but is not limited to operating systems, command line user interfaces, conversational interfaces, web-based user interfaces, zooming user interfaces, touch screens, task-based user interfaces, touch user interfaces, text-based user interfaces, intelligent user interfaces, brain-computer interfaces (BCIs), and graphical user interfaces, or any combination thereof. The system 400 may present data of the user interface to the user 405 via a display 316 operably connected to the processor 220. A display 316 may be defined as an output device that communicates data that may include, but is not limited to, visual, auditory, cutaneous, kinesthetic, olfactory, and gustatory, or any combination thereof.

In a preferred embodiment, a control board of the display 316 receives image data 425C from the first computing device 410A and second computing device 510. The control board may then present said image data 425C via the display 316 in a plurality of display windows 705 of the display user interface 711. In a preferred embodiment, the image data 425C is streamed from the first computing device 410A and second computing device 510 to the control board, wherein the control board inserts said streamed image data 425C into said plurality of display windows 705. Alternatively, the control board may automatically select a layout of the display user interface 711, wherein said layout may be determined based on a plurality of variables, including, but not limited to, number of patient data selected, type of patient data selected, user preferences, patient preferences, user location, patient location, device type, or any combination thereof. For instance, the control board may select a layout of a display user interface 711 comprising a split screen having two display windows 705 imitating phone screens when the system 400 detects a phone of a healthcare professional and a phone of a patient being used to review patient data 425B, as illustrated in FIG. 7.

Alternatively, the control board may manipulate the image data 425C and/or plurality of display windows 705 based on commands received from an input device. In one preferred embodiment, the display user interface 711 may also comprise a control window, which may allow a user 405 to control the layout of the display user interface 711. For instance, a user 405 may choose to layout that separates the display user interface 711 of four separate display windows 705, as illustrated in FIG. 9. Alternatively, an input device having a plurality of layouts thereon may be used to manipulate the layout of the display user interface 711. The input device may be connected to the system 400 via a wired or wireless connection. In a preferred embodiment, the input device communicates commands to the control board, which the control board uses to manipulate the image data 425C and/or plurality of display windows 705.

In some preferred embodiments, indicia within the first user interface 411A, access user interface 411B, second user interface 511, and/or display user interface 711 may be used to indicate various commands to be executed by the processor 220 and/or data of the system 400. In a preferred embodiment, indicia used within the first user interface 411A and second user interface 511 indicate the various types of patient data 425B to be presented within the display user interface 711. For instance, a user 405 may be required to select four different types of patient data 425B from a selection screen of the patient's user interface, which the system 400 may present via the display 316. The system 400 may use indicia to indicate which categories of patient data 425B are available for review, which may be decided based on permissions of the system 400. In another preferred embodiment, indicia may be used to indicate which type of layout should be used by the display user interface 711 to present the patient data 425B thereon. For instance, a user 405 may manipulate the input device in a way that commands the control board to select an indicia representing a layout having five display windows 705 representing cell phone screens, wherein the image data 425C presented in the five display windows 705 of the display user interface 711 corresponds with the image data 425C of a healthcare professional's computing device, wherein the image data 425C corresponds to patient data 425B selected by the healthcare provider via the user interface of their computing device.

In yet another preferred embodiment, the display user interface 711 may further comprise a communication window, which may allow a user 405 to remotely communicate with other users 405 of the system 400 while presenting patient data 425B. For instance, a video feed captured by a camera of the first computing device 410A and second computing device 510 may be presented in a communication window of a display user interface 711 of a first display 316 and second display 316 along with any data within the plurality of display windows 705, wherein the plurality of display windows 705 of the display user interface 711 of the said second display 316 are configured to mirror data of the plurality of display windows 705 of said first display 316. This may allow a healthcare professional to remotely interact with patients and/or other healthcare professionals while reviewing a patient's patient data 425B. For instance, a first healthcare professional and second healthcare professional collaborating in the treatment of a patient may want to simultaneously meet with a patient even when the second healthcare professional is unable to be physically present with the first healthcare professional and patient. By way of a second video feed transmitting data to a communication window of a the first display user interface 711 of a first display 316 in the presence of said first healthcare professional and patient and a first video feed transmitting data to a communication window of a second display user interface 711 of a second display 316 in the presence of the second healthcare provider, the first healthcare provider, second healthcare provider, and patient may all see the same data on their respective computing device as well as a live stream of each other so that they may collaborate. Therefore, the communication window may be used by the system 400 in multiple ways without departing from the inventive subject matter as described herein.

Information presented via a display 316 may be referred to as a soft copy of the information because the information exists electronically and is presented for a temporary period of time. Information stored on the non-transitory computer-readable medium 416 may be referred to as the hard copy of the information. For instance, a display 316 may present a soft copy of visual information via a liquid crystal display (LCD), wherein the hardcopy of the visual information is stored on a local hard drive. For instance, a display 316 may present a soft copy of audio information via a speaker, wherein the hard copy of the audio information is stored in RAM. For instance, a display 316 may present a soft copy of tactile information via a haptic suit, wherein the hard copy of the tactile information is stored within a database 115. Displays 316 may include, but are not limited to, cathode ray tube monitors, LCD monitors, light emitting diode (LED) monitors, gas plasma monitors, screen readers, speech synthesizers, haptic suits, virtual reality headsets, speakers, and scent generating devices, or any combination thereof.

In some preferred embodiments of the system, the system may be used by a user to track a quantity and/or condition of health inventory, such as medications, food, workout equipment, etc. For instance, a patient prescribed a particular diet by a physician may be sent food products that assist said patient to adhere to said particular diet. The patient may scan a barcode of the food product, and the data may be logged by the system. When the patient is visiting the doctor, this information may be accessible in a way that it may reviewed in the manners described herein. A user may manually or automatically update health inventory using a computing device, which may be saved by the system as health inventory data. In one preferred embodiment, health inventory data may be automatically uploaded to a user profiles once scanned by the user. In another preferred embodiment, health inventory data of a user profile may be updated when a user purchases health inventory from a third-party retailer via the user interface. The computing device hosting a user interface may be operably connected to a third-party retailer's point-of-sale system. When health inventory is purchased from a third-party retailer by the user via the user interface, the point-of-sale system may automatically transmit the health inventory data of the purchased health inventory to the system. The processor may then transfer the purchased health inventory data to the associated user profile.

In another preferred embodiment, the system may automatically add purchased health inventory data of purchased health inventory to a user profile based on the quantity of health inventory within the user profile compared to a lower limit, wherein said lower limit represents the lowest amount of health inventory a user may have before a purchase takes place. For instance, the system may automatically add purchased health inventory data pertaining to a patient's blood pressure medication acquired through a local pharmacy via the user interface to a user profile having a virtual representation of a patient's medication cabinet, wherein said medication cabinet has a low quantity of blood pressure medication when compared to the lower limit for quantity of blood pressure medication. For instance, the system may automatically add purchased health inventory data pertaining to food related to a particular diet of a patient acquired through a food delivery service via the user interface to a user profile having a virtual representation of a patient's cupboard, wherein said cupboard has a low quantity of food related to a particular diet when compared to the lower limit for said food related to a particular diet. The computing device may be operably connected to a third-party retailer's point-of-sale system via the Bluetooth, Wi-Fi, or other such transceiver, but is not limited to these methods of communication.

In one preferred embodiment, the system 400 may use artificial intelligence (AI) techniques to assist healthcare professionals in the presentation of patient data 425B to a patient. The term "artificial intelligence" and grammatical equivalents thereof are used herein to mean a method used by the system 400 to correctly interpret and learn from data of the system 400 or a fleet of systems in order to achieve specific goals and tasks through flexible adaptation. Types of AI that may be used by the system 400 include, but are not limited to, machine learning, neural network, computer vision, or any combination thereof. The system 400 preferably uses machine learning techniques to discern which patient data 425B of a patient's user profile 425 is relevant to a particular visit to a healthcare facility, wherein the instructions carried out by the processor 220 for said machine learning techniques are stored on the CRM, server 110, and/or database 115. Machine learning techniques that may be used by the system 400 include, but are not limited to, regression, classification, clustering, dimensionality reduction, ensemble, deep learning, transfer learning, reinforcement learning, or any combination thereof.

The system 400 may use more than one machine learning technique to discern which patient data 425B in a patient's user profile 425 might be relevant for a particular visit to a healthcare facility. For instance, the system 400 comprising a microphone may use a combination of natural language processing and reinforcement learning to discern which areas of a patient's CAT scan in one of a plurality of display windows 705 of the display user interface 711 a healthcare professional is currently referring to and subsequently manipulate the image data 425C to focus on that particular area. When the system 400 determines that the healthcare professional is no longer focusing on that particular area of the CAT scan, the system 400 may revert the image data 425C to its form prior to the manipulation. In some preferred embodiments, the system 400 may use machine learning techniques to deduce potential concerns about a patient's medical data that might be indicative a certain medical condition. Once the potential medical condition has been determined, the system 400 may present the information to the user interface of the healthcare professionals so that the healthcare professional may determine whether to discuss said potential medical conditions with the patient. For instance, the system 400 may determine that certain EKG readings are indicative of an enlarged heart and make this known only to the healthcare professional via the user interface of the healthcare professional's mobile computing device. However, the healthcare professional may mentally note that a patient may have an undiagnosed anxiety disorder that could also cause similar EKG readings and subsequently require additional testing before making such potential condition known to the patient.

To prevent un-authorized user 405 from accessing other user's 405 information, the system 400 may employ a security method. As illustrated in FIG. 10, the security method of the system 400 may comprise a plurality of permission levels 1000 that may grant users 405 access to user content 1015, 1035, 1055 within the database 115 while simultaneously denying users 405 without appropriate permission levels 1000 the ability to view user content 1015, 1035, 1055. To access the user content 1015, 1035, 1055 stored within the database 115, users 405 may be required to make a request via a user interface. Access to the data within the database 115 may be granted or denied by the processor 220 based on verification of a requesting user's 1005, 1025, 1045 permission level 1000. If the requesting user's 1005, 1025, 1045 permission level 1000 is sufficient, the processor 220 may provide the requesting user 1005, 1025, 1045 access to user content 1015, 1035, 1055 stored within the database 115. Conversely, if the requesting user's 1005, 1025, 1045 permission level 1000 is insufficient, the processor 220 may deny the requesting user 1005, 1025, 1045 access to user content 1015, 1035, 1055 stored within the database 115. In an embodiment, permission levels 1000 may be based on user roles 1010, 1030, 1050 and administrator roles 1070, as illustrated in FIG. 10. User roles 1010, 1030, 1050 allow requesting users 1005, 1025, 1045 to access user content 1015, 1035, 1055 that a user 405 has uploaded and/or otherwise obtained through use of the system 400. Administrator roles 1070 allow administrators 1065 to access system 400 wide data.

In an embodiment, user roles 1010, 1030, 1050 may be assigned to a user in a way such that a requesting user 1005, 1025, 1045 may view user profiles 425 containing user data 425A, patient data 425B, and image data 425C via a user interface. To access the data within the database 115, a user 405 may make a user request via the user interface to the processor 220. In an embodiment, the processor 220 may grant or deny the request based on the permission level 1000 associated with the requesting user 1005, 1025, 1045. Only users 405 having appropriate user roles 1010, 1030, 1050 or administrator roles 1070 may access the data within the user profiles 425. For instance, as illustrated in FIG. 10, requesting user 1 1005 has permission to view user 1 content 1015 and user 2 content 1035 whereas requesting user 2 1025 only has permission to view user 2 content 1035. Alternatively, user content 1015, 1035, 1055 may be restricted in a way such that a user may only view a limited amount of user content 1015, 1035, 1055. For instance, requesting user 3 1045 may be granted a permission level 1000 that only allows them to view user 3 content 1055 related to their specific healthcare records but not user 3 content 1055 related to other their healthcare records. In the example illustrated in FIG. 10, an administrator 1065 may bestow a new permission level 1000 on users so that it may grant them greater permissions or lesser permissions. For instance, an administrator 1065 may bestow a greater permission level 1000 on other users so that they may view user 3's content 1055 and/or any other user's 405 content 1015, 1035, 1055. Therefore, the permission levels 1000 of the system 400 may be assigned to users 405 in various ways without departing from the inventive subject matter described herein.

FIG. 11 provides a flow chart 1100 illustrating certain, preferred method steps that may be used to carry out the method of securely logging a user 405 into an access computing device 410B by way of a first computing device 410A and a predefined pattern 605. Step 1105 indicates the beginning of the method. During step 1110, a first computing device 410A may accept input data from a user 405 via an input device. The first computing device 410A may then perform a query to determine whether the input data matches first login credentials of user data 425A within the user's 405 user profile 425 during step 1115. Based on the results of the query, the first computing device 410A may take an action during step 1120. If the input data matches the first login credentials of the user data 425A of a user profile 425, the system 400 may activate a camera of the first computing device 410A and present a scanning screen to said user 405 during step 1125. If the input data does not match the first login credentials of the user data 425A of a user profile 425, the system 400 may return to step 1110.

After presenting the scanning screen and accessing the camera, the first computing device 410A may accept image data 425C from the camera during step 1130. During step 1135, the first computing device 410A may perform a query to determine whether image data 425C matches a predefined pattern 605, wherein said predefined pattern 605 contains second login credentials of an access computing device 410B. Based on the results of the query, the first computing device 410A may perform an action during step 1140. If the first computing device 410A determines that the image data 425C does not match a predefined pattern 605 of the system 400, the first computing device 410A may return to step 1130. If the first computing device 410A determines that the image data 425C does match a predefined image of the system 400, the first computing device 410A may send a computer readable signal to the access computing device 410B containing both the first login credentials and second login credentials during step 1145. The system 400 may then proceed to the terminate method step 1150.

FIG. 12 provides a flow chart 1200 illustrating certain, preferred method steps that may be used to carry out the method of an access computing device 410B allowing access to a database 115. Step 1205 indicates the beginning of the method. During step 1210, the processor 220 may receive a computer readable signal from a first computing device 410A, wherein said computer readable signal contains first login credentials, second login credentials, and an identifying address of the first computing device 410A. The processor 220 may then perform a query during step 1215 to determine whether or not the first login credentials, second login credentials, and identifying address match known login credentials and identifying address of the system 400. Based on the results of the query, the system 400 may perform an action during step 1220. If the processor 220 determines that even one of the first login credential and second login credential do not match known login credentials of the system 400, the processor 220 may proceed to the terminate method step 1230. If the processor 220 determines that both the first login credential and second login credential match known login credentials of the system 400, the processor 220 may access the database 115 and allow a user 405 to access files of said database 115 via a user interface during step 1225. The system 400 may then proceed to terminate method step 1230.

FIG. 13 provides a flow chart 1300 illustrating certain, preferred method steps that may be used to carry out the method of presenting patient data 425B received from a first computing device 410A and second computing device 510 in a plurality of display windows 705 of a display user interface 711. Step 1305 indicates the beginning of the method. During step 1307, the processor 220 may perform a query to determine if a first computing device 410A and second computing device 510 are in communication with said processor 220. Based on the results of the query, the processor 220 may perform an action during step 1310. If the processor 220 determines that a first computing device 410A and second computing device 510 are connected to said processor 220, the processor 220 may proceed to step 1315. If the processor 220 determines that a first computing device 410A and second computing device 510 are not connected, the processor 220 may proceed to terminate method step 1345. During step 1315, the processor 220 may present a display user interface 711 via the display 316. The processor 220 may then receive image data 425C from a first computing device 410A and/or second computing device 510 during step 1320. The processor 220 may perform a query to determine if a number of display windows of a plurality of display windows 705 is equal to the number of image data 425C during step 1325. Based on the results of the query, the processor 220 may take an action during step 1330. If the processor 220 determines that a number of display windows is the same as the number of image data 425C, the processor 220 may return to step 1307. If the processor 220 determines that the number of display windows is the same as the number of image data 425C, the processor 220 may proceed to step 1335.

During step 1335, the processor 220 may perform a query to determine whether a display window of said plurality of display windows 705 should be added or subtracted to said display user interface 711 based on a number of image data 425C received by the processor 220 from the first computing device 410A and second computing device 510 and compared to a current number of display windows of the display user interface 711. Based on the results of the query, the processor may perform an action during step 1340. If the processor 220 determines a display window must be added to the display user interface 711 so that a number of display windows equals the number of image data 425C, the processor 220 may proceed to step 1342 and subsequently add an additional display window to said plurality of display windows 705. If the processor 220 determines a display window must be subtracted from the display user interface 711 so that a number of display windows equals the number of image data 425C, the processor 220 may proceed to step 1343 and subsequently remove a display window from said plurality of display windows 705. Once the number of display windows has been altered, the system 400 may return to step 1307 and repeat the process until the first computing device 410A and second computing device 510 are no longer in communication with said processor 220.

The subject matter described herein may be embodied in systems, apparati, methods, and/or articles depending on the desired configuration. In particular, various implementations of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that may be executable and/or interpretable on a programmable system including at least one programmable processor, which may be special or general purpose, coupled to receive data and instructions from, and to transmit data and instructions to, a storage system, and at least one peripheral device.

These computer programs, which may also be referred to as programs, software, applications, software applications, components, or code, may include machine instructions for a programmable processor, and may be implemented in a high-level procedural and/or object-oriented programming language, and/or in assembly machine language. As used herein, the term "non-transitory computer-readable medium" refers to any computer program, product, apparatus, and/or device, such as magnetic discs, optical disks, memory, and Programmable Logic Devices (PLDs), used to provide machine instructions and/or data to a programmable processor, including a non-transitory computer-readable medium that receives machine instructions as a computer-readable signal. The term "computer-readable signal" refers to any signal used to provide machine instructions and/or data to a programmable processor. To provide for interaction with a user, the subject matter described herein may be implemented on a computer having a display device, such as a cathode ray tube (CRD), liquid crystal display (LCD), light emitting display (LED) monitor for displaying information to the user and a keyboard and a pointing device, such as a mouse or a trackball, by which the user may provide input to the computer. Displays may include, but are not limited to, visual, auditory, cutaneous, kinesthetic, olfactory, and gustatory displays, or any combination thereof.

Other kinds of devices may be used to facilitate interaction with a user as well. For instance, feedback provided to the user may be any form of sensory feedback, such as visual feedback, auditory feedback, or tactile feedback; and input from the user may be received in any form including, but not limited to, acoustic, speech, or tactile input. The subject matter described herein may be implemented in a computing system that includes a back-end component, such as a data server, or that includes a middleware component, such as an application server, or that includes a front-end component, such as a client computer having a graphical user interface or a Web browser through which a user may interact with the system described herein, or any combination of such back-end, middleware, or front-end components. The components of the system may be interconnected by any form or medium of digital data communication, such as a communication network. Examples of communication networks may include, but are not limited to, a local area network ("LAN"), a wide area network ("WAN"), metropolitan area networks ("MAN"), and the internet.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For instance, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, devices, and arrangements of the parts and method stages which have been described and illustrated in order to explain the nature of this inventive subject matter can be made without departing from the principles and scope of the inventive subject matter.

What is claimed is:

1. A system for presenting data related to a patient's health comprising:
   a first computing device having a first user interface,
      wherein said first computing device is configured to connect to a user profile of a healthcare provider,
   a second computing device having a second user interface,
      wherein said second computing device is configured to connect to said user profile of a patient,
      wherein said user profile of said patient contains patient data,
   a display having a control board operably connected to said first computing device and said second computing device,
      wherein a processor of said control board is configured to receive first image data from said first computing device,
      wherein a processor of said control board is configured to receive second image data from said second computing device,
      wherein said processor of said control board organizes said first image data and said second image data in a plurality of display windows of a display user interface of said display,
   a communication interface operably connected to said control board,
      wherein an input device transmits commands to said control board via said communication interface,
      wherein said commands instruct said processor as to a layout of said display user interface based on said first image data and said second image data, and
   a non-transitory computer-readable medium coupled to said processor,
      wherein said non-transitory computer-readable medium contains instructions stored thereon, which, when executed by said processor, cause said processor to perform operations comprising:
         receiving said first image data,
         receiving said second image data,
         determining said layout of said layout of said display user interface based on at least one of said commands, first image data, and second image data,
         creating mirrored image data based on said display user interface, first image data, and second image data, and
         transmitting said mirrored image data to a database.

2. The system of claim 1, further comprising a secondary security device operably connected to said control board,
   wherein said secondary security device is configured to only communicate with said control board of said display.

3. The system of claim 2, wherein said secondary security device is configured to collect biometric data from a user, wherein said biometric data is used by said control board to verify login credentials of said user, wherein said login credentials allow said user to access said display user interface of said display.

4. The system of claim 3, further comprising additional instructions stored on said non-transitory computer-readable medium, which, when executed by said processor, cause said processor to perform additional operations comprising:
   receiving said biometric data from said secondary security device,
   checking said biometric data against said login credentials, and
   activating said display when said biometric data matches said login credentials.

5. The system of claim 2, wherein said secondary security device is configured to send a computer readable signal to said control board, wherein said computer readable signal is used by said control board to verify login credentials of a user, wherein said login credentials allow said user to access said display user interface of said display.

6. The system of claim 5, further comprising additional instructions stored on said non-transitory computer-readable medium, which, when executed by said processor, cause said processor to perform additional operations comprising:
   receiving said computer readable signal from said secondary security device,
   checking said computer readable signal against said login credentials,
   activating said display when said computer readable signal matches said login credentials, and
   displaying an indicia on said display to indicate when said computer readable signal does not match said login credentials.

7. The system of claim 1, wherein said input device is at least one of a camera and microphone connected to at least one of said first computing device and second computing device,
   wherein said camera is configured to collect video data of at least one of said healthcare provider and said patient,
   wherein said microphone is configured to collect audio data of at least one of said healthcare provider and said patient.

8. The system of claim 7, further comprising a communication window of said display user interface,
   wherein at least one of said video data and said audio data are presented within said communication window to facilitate communication between said healthcare provider and said patient.

9. The system of claim 8, further comprising additional instructions stored on said non-transitory computer-readable medium, which, when executed by said processor, cause said processor to perform additional operations comprising:
   receiving said video data from at least one of said first computing device and second computing device,
   receiving said audio data from at least one of said first computing device and second computing device, and streaming at least one of said video data and said audio data to said communication window.

10. The system of claim 8, wherein said control board uses natural language processing to transform said audio data into input data, wherein said control board manipulates said layout based on said input data.

11. The system of claim 1, wherein said control board determines a window number of said display user interface, wherein said window number is a total of said first image data and second image data, wherein said control board manipulates said layout based on said window number, wherein said window number determines an amount of said plurality of display windows.

12. The system of claim 1, wherein at least one of said first user interface and said second user interface is operably connected to a point-of-sale system of a third-party.

13. The system of claim 12, further comprising additional instructions stored on said non-transitory computer-readable medium, which, when executed by said processor, cause said processor to perform additional operations comprising:
    displaying patient data on at least one of said first computing device and second computing device operably connected to said point-of-sale system, and
    purchasing health supplies via said point-of-sale system when a quantity of said health supplies has dropped below a lower limit.

* * * * *